United States Patent [19]
Monfre et al.

[11] Patent Number: 5,793,545
[45] Date of Patent: Aug. 11, 1998

[54] OPTICAL SPECTRAL FILTER AND LINEAR POSITIONER THEREFOR

[75] Inventors: Stephen L. Monfre, Plainville; Anthony C. Jeannotte, Foxboro, both of Mass.; Richard H. Seager, Mystic, Conn.; Norman P. Bridges, Cedar Park, Tex.; Robert E. Johnson, Pembroke, Mass.

[73] Assignee: The Foxboro Company, Foxboro, Mass.

[21] Appl. No.: 740,287

[22] Filed: Oct. 25, 1996

[51] Int. Cl.⁶ .......................................... G02B 5/22
[52] U.S. Cl. ................. 359/891; 359/350; 359/889; 250/339.01; 250/339.07; 356/419
[58] Field of Search ....................... 359/885, 889, 359/891, 892, 350, 578, 587, 590; 250/339.01, 339.07; 356/419

[56] References Cited

U.S. PATENT DOCUMENTS 5,448,070  9/1995  Day et al. ................. 250/339.13
5,508,525  4/1996  Day et al. ................. 250/339.07
5,519,219  5/1996  Alexay et al. ............. 250/339.07

OTHER PUBLICATIONS

Laboratory Application Data for MIRAN IR Analyzers, The Foxboro Company, 1991.

*Primary Examiner*—Jon W. Henry
*Assistant Examiner*—Darren E. Schuberg
*Attorney, Agent, or Firm*—David Barron; Jules Jay Morris; Terrence Martin

[57] ABSTRACT

A multi-wavelength optical filter for a portabe gas analyzer includes a filter assembly having a first opening and multiple additional openings. The first opening has a linearly variable filter disposed therein, while the additional openings have discrete filters disposed therein. The filters are linearly aligned, such that filter selection is facilitated by using the filter assembly with a linear positioning mechanism.

18 Claims, 10 Drawing Sheets

OPTICAL SPECTRAL FILTER AND LINEAR POSITIONER THEREFOR

TECHNICAL FIELD

The present invention relates, in general, to optical spectral filtering. More specifically, the present invention relates to a selectable wavelength optical filter and associated positioning mechanism therefor.

BACKGROUND OF THE INVENTION

Optical spectral analysis is conventionally performed by analyzing the spectrum of a particular substance (for example, gasses, liquids, solids and plasmas). One technique for performing optical spectral analysis includes sequentially passing a number of selected wavelength light beams through a substance to be analyzed (for example, a gas), and measuring the intensity of each wavelength after it passes through the substance. Their intensities are then used to determine quantitative or qualitative properties of the substance.

Detecting a wide variety of substances requires a wide variety of different wavelength light sources. In practice, different wavelength light sources have been generated using a broadband light source that is passed through different selectable spectral bandpass filters.

In one previous example, a filter wheel having a predetermined number of discrete bandpass filters is used in combination with a broadband light source to produce a number of selectable wavelength light sources. However, this solution is physically limited by the number of discrete filters that can be disposed on a single filter wheel. Thus, the practical number of available wavelengths is quite limited by this technique.

Another technique for producing a range of different wavelength light sources is shown in FIG. 1, and is used in the "Miran 1B Gas Analyzer" from The Foxboro Company of Foxboro, Mass., USA. A filter wheel assembly 11 includes a filter wheel 13 mounted on a rotationally positionable shaft 21. Mounted within filter wheel 13 are three semi-circular variable filters 15, 17, and 19. Filter 15 has a passband range from 2.5 microns to 4.5 microns, filter 17 has a range from 4.5 microns to 8 microns, and filter 19 has a range from 8 microns to 14 microns. Thus, a continuous range of wavelengths from 2.5 microns to 14 microns is selectable. Unfortunately, semicircular variable filters have a relatively high cost, and a restricted wavelength range (thus requiring three separate filters in this example). Accordingly, filter wheel assembly 11 is a relatively expensive solution to achieving a wide range of selectable wavelengths.

The present invention is directed toward a solution to the above problems. That is, the present invention is directed toward a selectable wavelength filter and positioning mechanism that has a relatively low cost, while still providing a wide enough variety of selectable wavelengths to facilitate a range of spectral analysis tasks.

SUMMARY OF THE INVENTION

In a first aspect, the present invention includes a multi-wavelength optical filter comprising a filter assembly that includes a variable frequency filter and a discrete frequency filter. The filter assembly has at least two openings with the variable frequency filter disposed in a first opening of the at least two openings. The discrete frequency filter is disposed in an additional opening of the at least two openings.

As an enhancement, a positioning mechanism may be connected to the filter assembly for selective positioning thereof. The positioning mechanism may include a position sensor for providing positional feedback used in selectively positioning the filter assembly.

As a further enhancement, the first opening and the additional opening may be linearly aligned. Furthermore, the openings may be substantially rectilinear in shape, and the variable frequency filter may be a linearly variable filter. Moreover, the filter assembly may include multiple additional openings, each being linearly aligned with the other and being similarly shaped. At least some of the additional openings may have discrete frequency filters disposed therein.

To summarize, through a selective combination of a linearly variable filter and several discrete filters on a positionable filter assembly, a spectral analysis system with a wide range of qualitative and quantitative detection abilities may be constructed. Furthermore, due to the use of fewer variable frequency filters than previously used, as supplemented with low-cost discrete filters, a more economic multi-wavelength filter assembly is created. Moreover, the linear positioning system disclosed herein permits precise positioning of the filter assembly, thereby achieving precise wavelength selection (particularly within the LVF filter section).

BRIEF DESCRIPTION OF THE DRAWINGS

The subject matter regarded as the present invention is particularly pointed out and distinctly claimed in the concluding portion of the specification. The invention, however, both as to organization and method of practice, together with further objects and advantages thereof, may best be understood by reference to the following detailed description taken in conjunction with the accompanying drawings in which:

DETAILED DESCRIPTION OF THE PREFERRED EMBODIMENT

Figure 2:
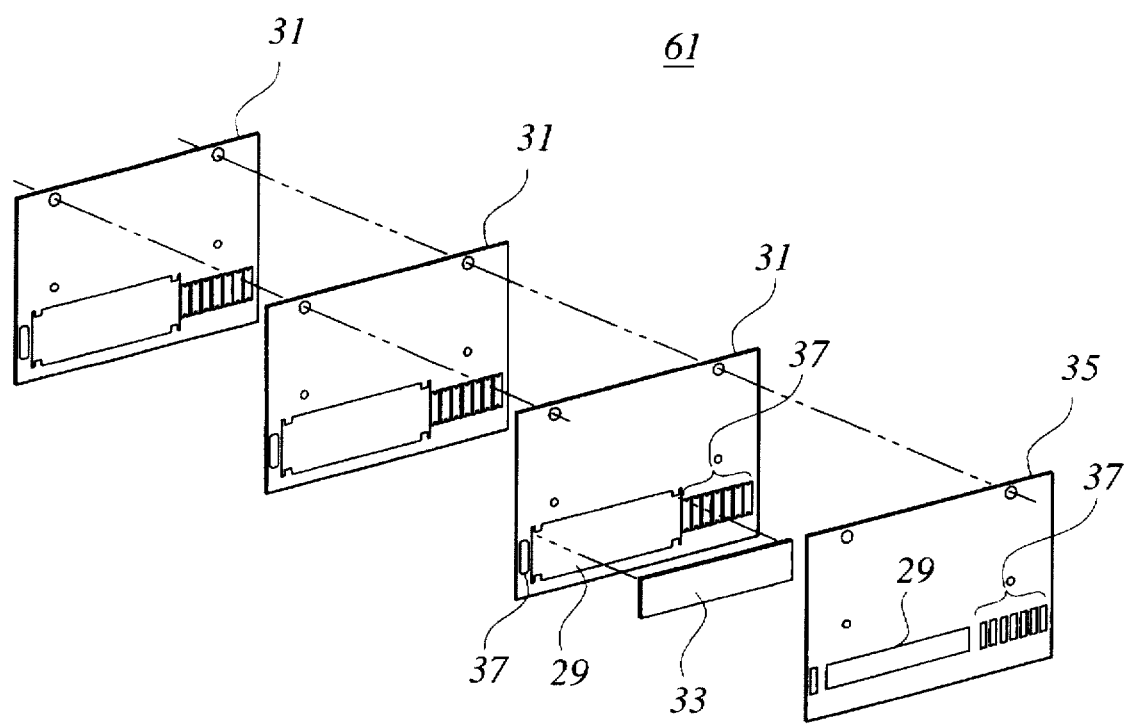
FIG. 2 is an assembly drawing of a filter holder in accordance with one embodiment of the present invention.

Turning to FIG. 2, an assembly drawing of a filter assembly 61 is depicted. Three filter holders 31 are stacked to form a filter holder stack. Each of the three filter holders 31 is formed by etching 0.020 inch aluminum panels. In the present embodiment, a stack of three precisely etched filter holders 31 is a less expensive solution than a single, thicker, for example, stamped or etched filter holder.

Each filter holder has a linear variable filter ("LVF") opening 29 etched therein and several discrete filter openings 37 etched therein. Filter openings 29 and 37 are precisely etched to accommodate linear variable filter ("LVF") 33 and several discrete filters, respectively.

Filter assembly 61 also includes a precisely etched mask 35 formed from 0.008 inch thick beryllium-copper. In the current embodiment, an LVF mask opening 29' has dimensions of 41 millimeters by 6 millimeters to mask a filter size of 10 millimeters×43 millimeters. Discrete filter mask openings 37' have dimensions of 1.4 millimeters×6 millimeters to mask discrete filters of 2 millimeters×7 millimeters. According to the present invention, the filter openings and apertures (that is, mask openings) can be sized to suit various application and filtering needs.

Figure 3:
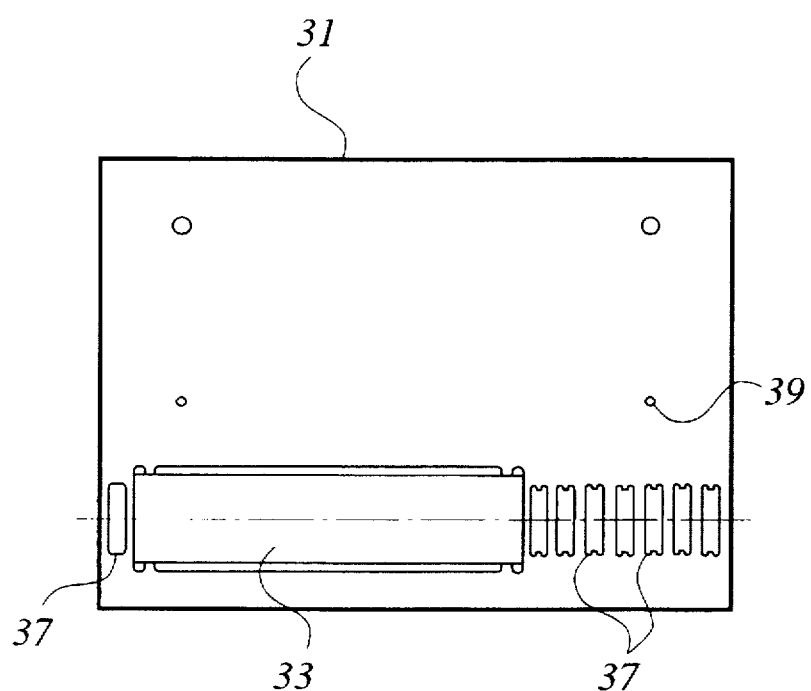
FIGS. 3–4 are assembly drawings of the filter holder of FIG. 2 during various stages of assembly.
Figure 4:
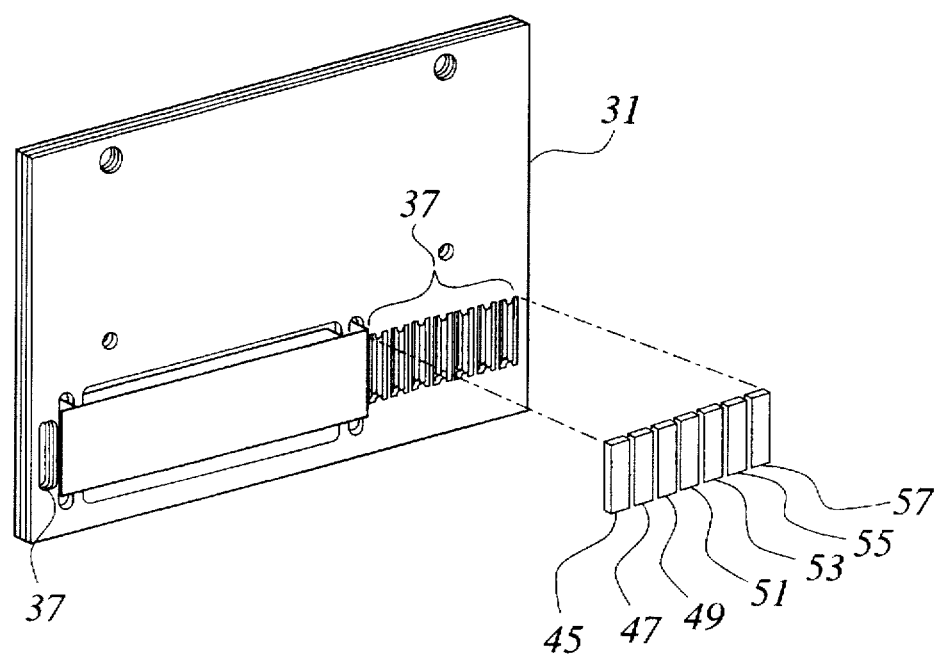

FIGS. 3-4 depict various stages of assembly of filter assembly 61. Turning to FIG. 3, LVF 33 has been mounted within the stack of filter holders 31 using an adhesive (for example, 3M brand, model 2216 adhesive). In other embodiments, other filter mounting schemes can be used including, for example, friction mounts, mechanical mounts, and additional masks used to hold the filters in place.

The stack of filter holders 31 and mask 35 includes an alignment hole 39 through which a pin later passes to precisely align filter holders 31 and mask 35.

Figure 1:
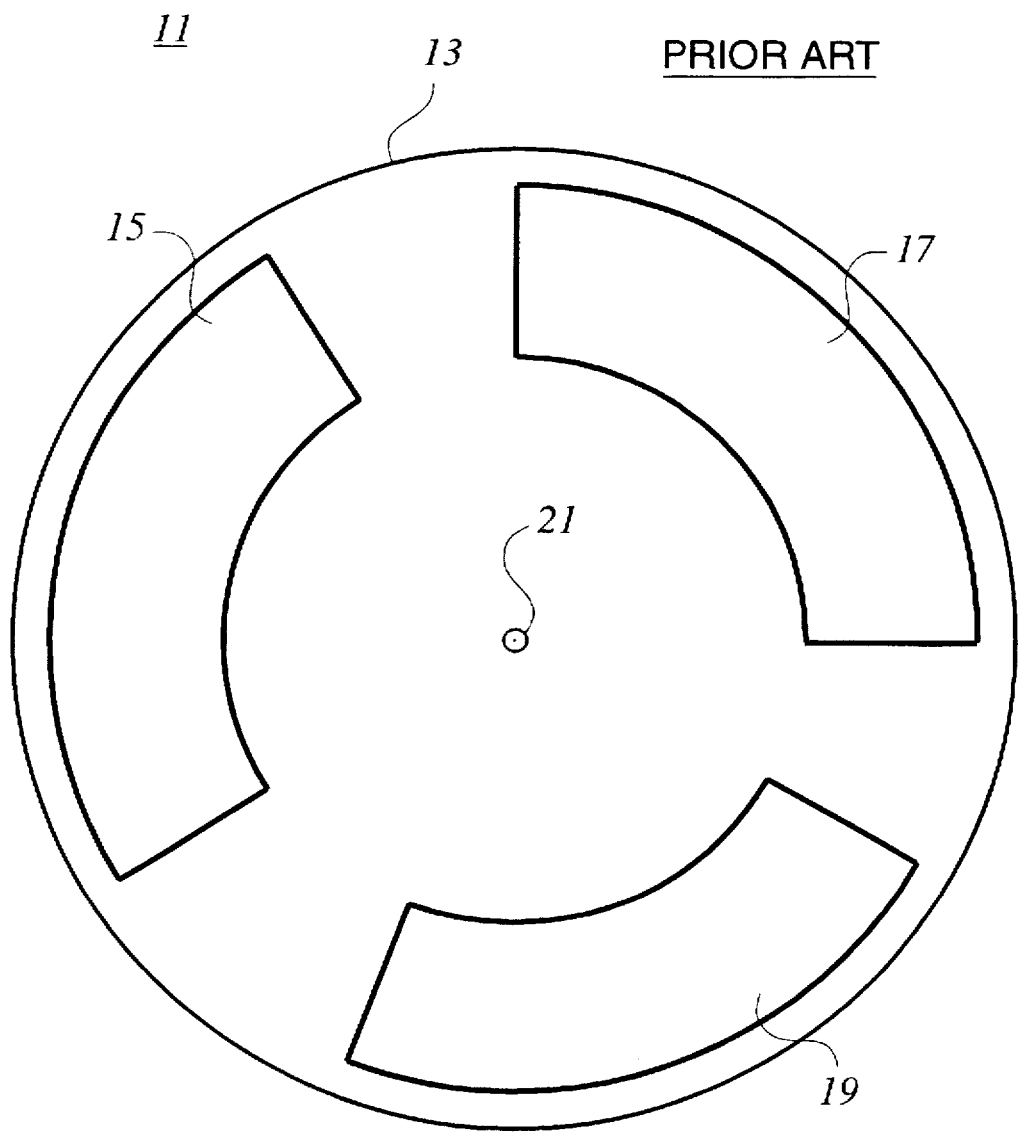
FIG. 1 is a diagram of a prior art filter assembly.

Turning to FIG. 4, discrete filters 45-57 are mounted in their respective discrete filter openings 37, again using an adhesive. Each of discrete filters 45-57 has a particular bandpass frequency for a given spectroscopy application. For example, the below table provides exemplary filter bandpass frequencies for a completed filter assembly 61. This combination of filters provides approximately 95% of the spectral identification abilities of the more expensive, three CVF filter assembly of FIG. 1.

| FILTER | PASSBAND |
| --- | --- |
| LVF 33 | 7.7 Microns–14.1 Microns |
| First Discrete Filter 45 | 1.86 Microns |
| Second Discrete Filter 47 | 3.33 Microns |
| Third Discrete Filter 49 | 3.57 Microns |
| Fourth Discrete Filter 51 | 4.00 Microns |
| Fifth Discrete Filter 53 | 4.25 Microns |
| Sixth Discrete Filter 55 | 4.5 Microns |
| Seventh Discrete Filter 57 | 4.62 Microns |

Each of the above-referenced filters is available from, for example, Optical Coating Laboratories Inc. of Santa Rosa, Calif., USA (filters are typically available in the 0.15 to 50 micron range).

Filter opening 37' does not have a filter within it. Operationally, this opening is used to pass the full spectrum of the light source used for testing and alignment purposes.

Figure 5:
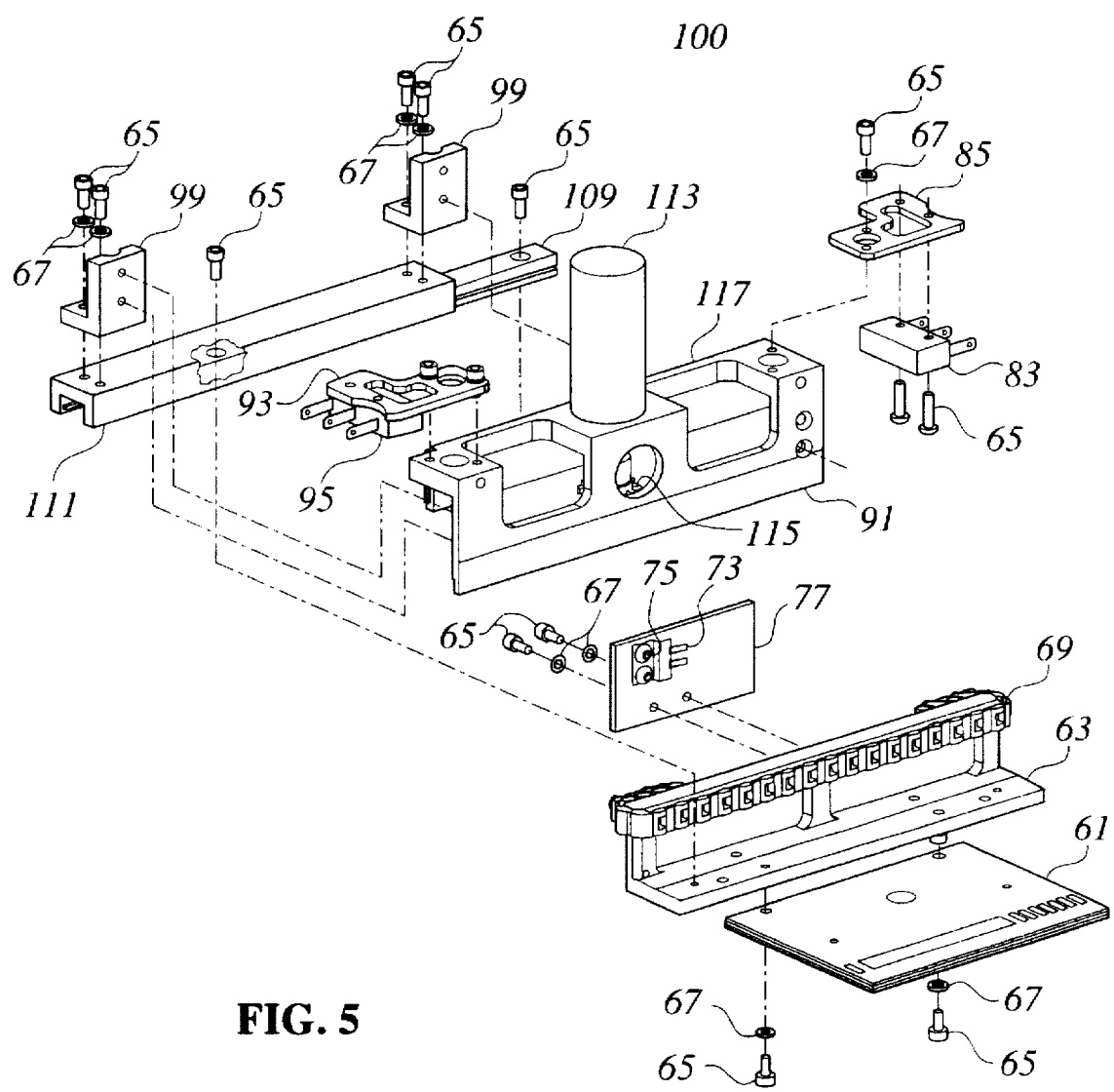
FIG. 5 is an assembly view of a filter positioning mechanism pursuant to one embodiment of the present invention.
Figure 7:
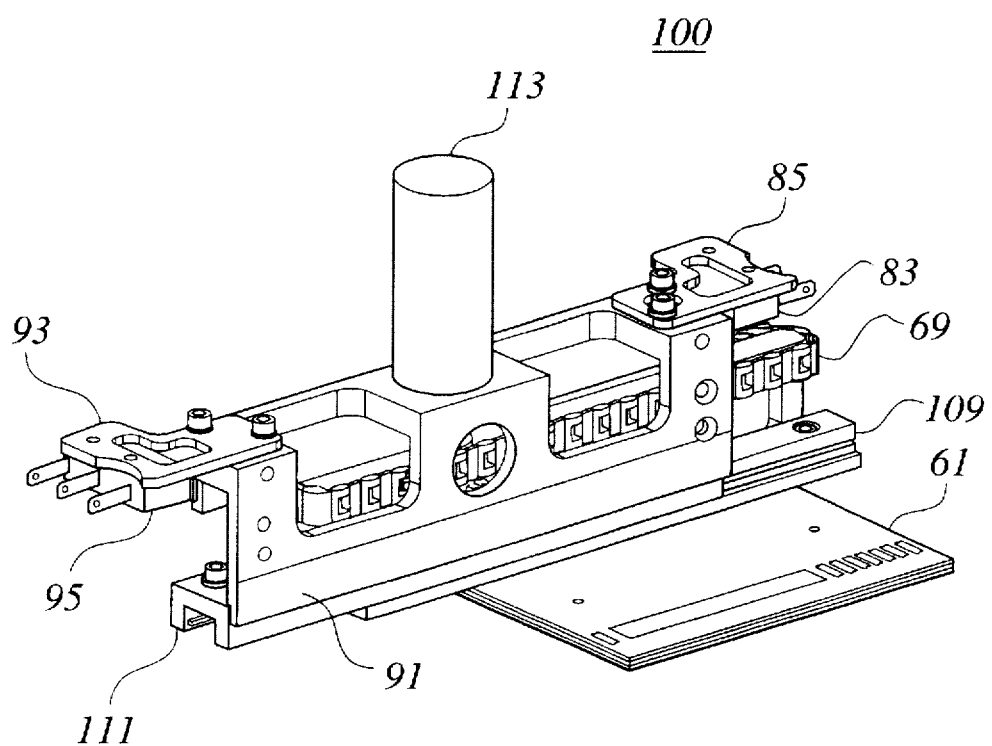
FIG. 7 is a perspective view of the filter positioning mechanism of FIG. 5.

Depicted in FIG. 5 is an assembly view of a linear positioner assembly 100 for filter assembly 61 according to the present invention (FIG. 7 depicts a completed perspective view of linear positioner assembly 100). Filter assembly 61 is attached to a filter translation assembly 63 using screws 65 and washers 67. Along the length of filter translation assembly 63 is a toothed belt 69 that operably engages gear 115 in the completed linear positioning assembly 100.

Figure 6:
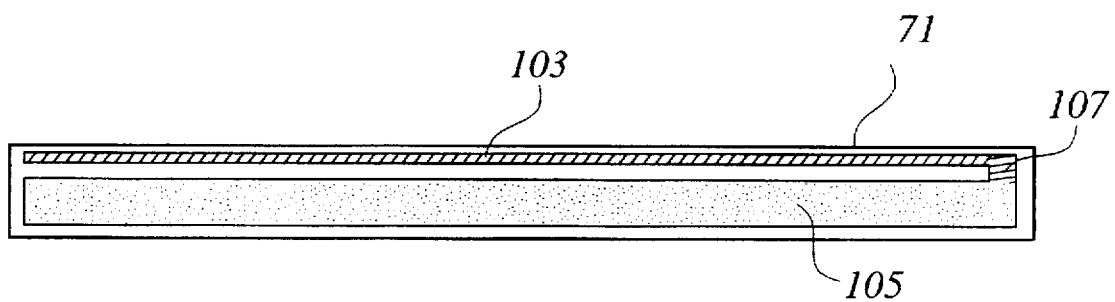
FIG. 6 is a resistor strip for use as a positional feedback mechanism for the positioning assembly of FIG. 5 in accordance with an embodiment of the present invention.

Disposed on a surface 117 of motor mount 91 is an adhesively secured resistor strip 71 (FIG. 6), that facilitates positional feedback. More specifically (referring temporarily to FIG. 6), resistor strip 71 includes a fully conductive strip 103, a resistive strip 105 and a conductive connection strip 107. Referring to FIG. 5, a potentiometer assembly 77 includes a wiper assembly 73 that operationally engages resistor strip 71 such that a resistance between two terminals 75 of wiper assembly 73 depends upon the position of filter translation assembly 63. More particularly, the two wipers of wiper assembly 73 contact conductive strip 107 and resistive strip 105 of resistor strip 71, respectively. Screws 65 and washers 67 secure potentiometer assembly 77 to filter translation assembly 63.

The combined filter assembly 61 and filter translation assembly 63 is secured to a carriage 109 using screws 65. Carriage 109 is, in turn, slidably mounted within a carriage housing 111. Carriage housing 111 is attached to motor mount 91 using carriage brackets 99, screws 65 and washers 67. When assembled, gear 115 of motor/gearbox assembly 113 engages tooth belt 69 such that filter assembly 61 is linearly positionable. Limit switches 83 and 95 are coupled to motor mount 91 using limit switch brackets 85 and 93 and provide end-of-travel indication to the system controlling the motion of filter assembly 100.

During operation, filter assembly 61 is linearly positioned by a control system coupled to motor/gearbox assembly 113, limit switches 83 and 95 and contacts 75 of wiper assembly 73. Many servo control schemes may be used to accurately position filter assembly 61 including, for example, a PID type control system/algorithm. Further, other mechanical positioning mechanisms are useful in accordance with the technique described herein and are to be considered part of the claimed invention.

Figure 8:
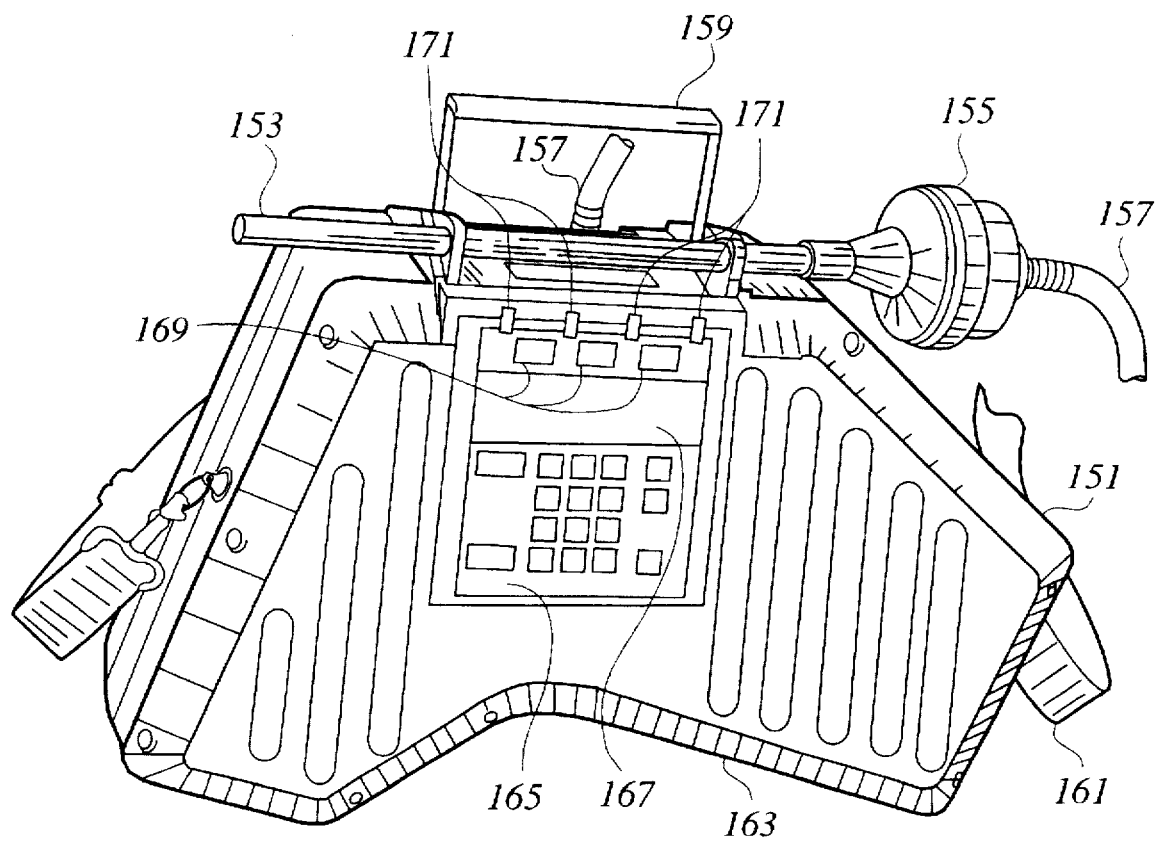
FIG. 8 is a perspective view of a portable gas analyzer utilizing the filter holder and positioning mechanism described herein in accordance with an embodiment of the present invention.

In accordance with the technique of the present invention, filter assembly 61 may be incorporated with other spectrographic componentry to form a portable gas analyzer in accordance with the present invention. Turning to FIG. 8, a portable gas analyzer 200 is shown. A housing 151 includes a conformally curved shape 163 such that when used in connection with a strap 161 and a handle 159, portable gas analyzer 200 may be operated while resting on the hip/waist of an operator. One hand of the operator supports the gas analyzer and operates keypad 165. More specifically, finger guides 171 protrude from housing 151 and facilitate location and operation of keys 169. Portable gas analyzer 200 is configured such that through use of keys 169 in connection with display 167 a majority of analysis functions can be performed. Thus, most operations of analyzer 200 can be achieved using the same hand to support and operate the analyzer 200.

The operator's other hand is used to hold a sniffing wand that includes a probe pipe 153, a filter holder 155, and a connection tubing 157, the connection tubing attached to and providing samples to the analyzer in housing 151.

Figure 9:
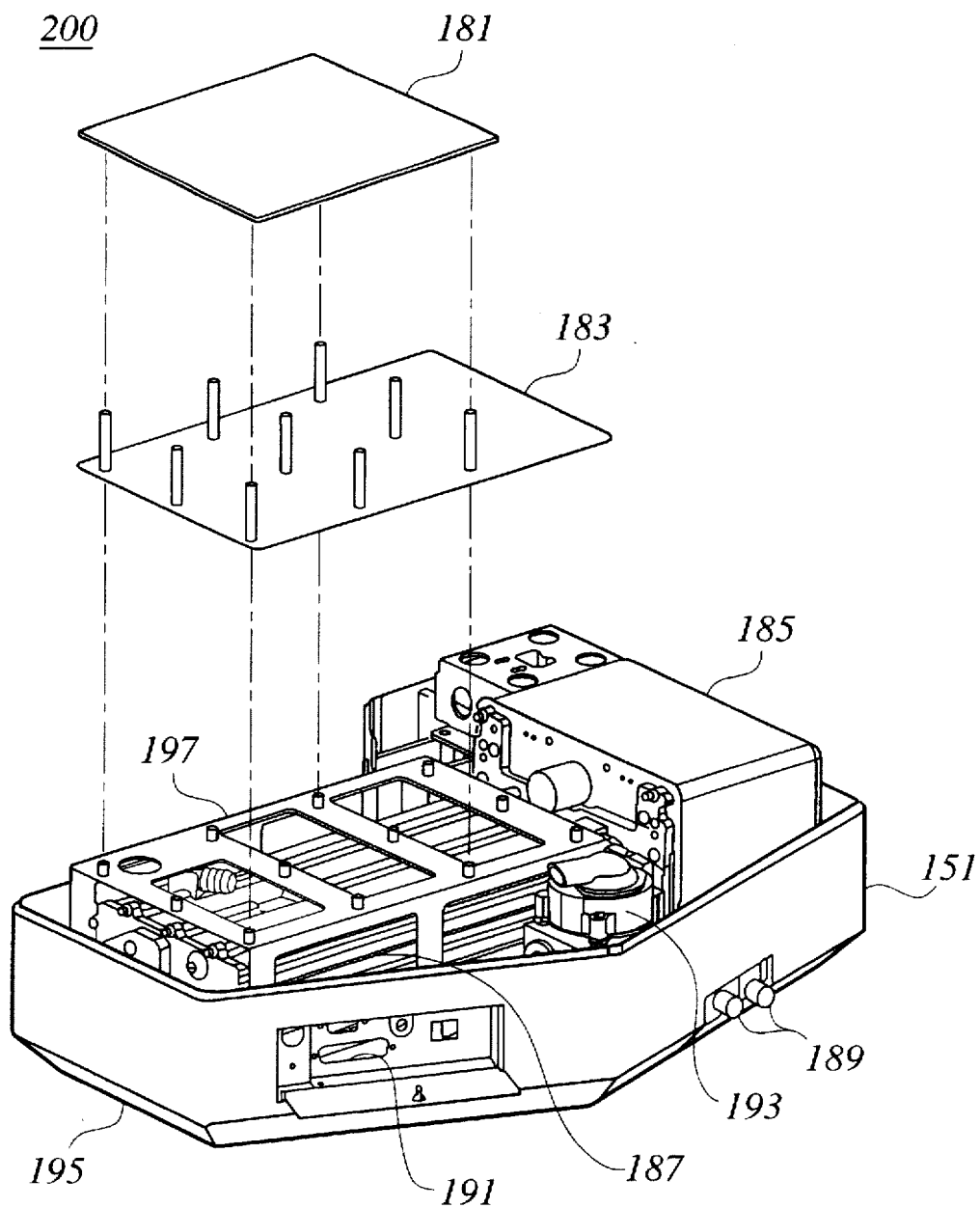
FIGS. 9 and 10 are assembly views of the internal components and layout of the portable gas analyzer of FIG. 8.

Turning to FIG. 9, an internal assembly drawing of gas analyzer 200 is depicted. Within housing 151 is a pump 193 used to draw gas from wand 157 through an inlet tube connector 189 (one of two connectors 189 is an inlet the other is an outlet). A spectrometer assembly 185 includes the filter positioning assembly of the present invention along with a wideband light source, light sensor, and chopper assembly. A chasis assembly 197 encloses a cell assembly 187 that contains mirrors used to increase the path length for spectrographic analysis.

Printed circuit cards 183 and 181 provide computational and control for portable gas analyzer 200. An I/O panel 191 facilitates connection of portable gas analyzer 200 to external devices such as, for example, printers and computers.

Figure 10:
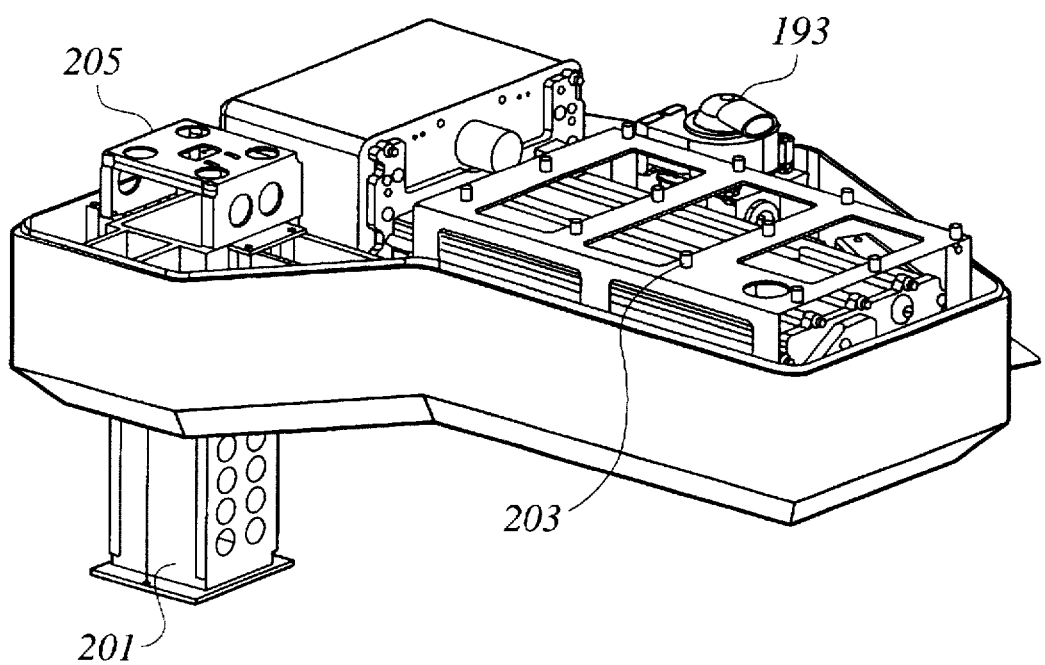

Turning to FIG. 10, portable gas analyzer 200 also includes chasis fasteners 203 for solidly mounting the chasis within housing 151. Furthermore, a battery connecting plate 205 is adapted to receive a battery pack assembly 201. Batterypack 201 is removable, and is field replaceable with alternate batterypacks. The door that facilitates access to batterypack 201 is secured with a screw to avoid inadvertent electrical connection/disconnection of batterypack 201 within a hostile and/or explosive environment.

The present invention has many advantages and features associated with it. Through a selective combination of a linearly variable filter and several discrete filters on a positionable filter assembly, a spectral analysis system with a wide range of qualitative and quantitative detection abilities may be constructed. Furthermore, due to the use of fewer variable frequency filters than previously used, as supplemented with low-cost discrete filters, a more economic multi-wavelength filter assembly is created. Moreover, the linear positioning system disclosed herein permits precise positioning of the filter assembly, thereby achieving precise wavelength selection (particularly within the LVF filter section).

While the invention has been described in detail herein, in accordance with certain preferred embodiments thereof, many modifications and changes thereto may be affected by those skilled in the art. Accordingly, it is intended by the appended claims to cover all such modifications and changes as fall within the true spirit and scope of the invention.

We claim:

1. A multi-wavelength optical filter comprising:
   a filter assembly having at least two openings;
   a variable frequency filter disposed in a first opening of said at least two openings; and
   a discrete frequency filter disposed in an additional opening of said at least two openings.

2. The filter of claim 1, further comprising a positioning mechanism connected to said filter assembly for selectively positioning said filter assembly.

3. The filter of claim 2, wherein said positioning mechanism includes a position sensor for providing positional feedback used in selectively positioning said filter assembly.

4. The filter of claim 1, further comprising at least one other discrete frequency filter disposed in a further additional opening of said at least two openings.

5. The filter of claim 1, wherein said first opening and said additional opening are linearly aligned.

6. The filter of claim 5, wherein said first opening is substantially rectilinear in shape, and said variable frequency filter comprises a linearly variable filter.

7. The filter of claim 6, wherein said additional opening is substantially rectilinear in shape.

8. The filter of claim 7, wherein said first opening has a longer side thereof being parallel to a direction of said linear alignment.

9. The filter of claim 8, wherein said additional opening has a longer side thereof being perpendicular to a direction of said linear alignment.

10. The filter of claim 9, wherein said filter assembly further comprises a plurality of additional openings, each additional opening being linearly aligned with said additional opening and being similarly shaped.

11. The filter of claim 10, wherein at least some of said plurality of additional openings have a discrete frequency filter disposed therein.

12. The filter of claim 11, wherein said linear alignment has a first end and a second end, and wherein said first opening is disposed toward said first end and at least some of said plurality of additional openings are disposed toward said second end.

13. The filter of claim 12, wherein most of said linearly variable filter and said discrete filters have bandpass frequencies within the infra-red band.

14. The filter of claim 6, further comprising a linear positioning mechanism coupled to said filter assembly for selective positioning thereof.

15. A multi-wavelength optical filter comprising:
   a filter assembly having a first opening and a plurality of additional openings;
   a variable frequency filter disposed in said first opening;
   at least some of said plurality of additional openings having discrete frequency filters disposed therein; and
   a positioning mechanism connected to said filter assembly for selectively positioning said filter assembly.

16. A multi-wavelength optical filter comprising:
   a filter assembly having a first opening and a plurality of additional openings;
   said first opening and said plurality of additional openings being substantially linearly aligned;
   said first opening having a substantially rectilinear shape with a longest dimension thereof being substantially parallel to said linear alignment;
   most of said plurality of additional openings being similarly substantially rectilinearly shaped and having a shortest dimension being substantially parallel to said linear alignment;
   a linearly variable frequency filter disposed in said first opening, said filter frequency changing along said linear alignment;
   at least some of said plurality of additional openings having discrete frequency filters disposed therein; and
   a linear positioning mechanism connected to said filter assembly for selectively positioning said filter assembly along said linear alignment.

17. The filter of claim 16, further in combination with a portable gas analyzer.

18. A portable gas analyzer comprising:
   a comformally curved housing for positioning against an operators waist;
   a keyboard for operation of the portable gas analyzer;
   a wand for drawing gas samples for analysis by the portable gas analyzer; and
   a multi-wavelength optical filter which comprises:
     a filter assembly having at least two openings;
     a variable frequency filter disposed in a first opening of said at least two openings; and
     a discrete frequency filter disposed in an additional opening of said at least two openings.

* * * * *